(12) United States Patent
Moidunny (10) Patent No.: US 12,091,020 B2
(45) Date of Patent: *Sep. 17, 2024

(54) METHOD AND SYSTEM FOR DRIVER POSTURE MONITORING

(71) Applicant: Harman International Industries, Incorporated, Stamford, CT (US)

(72) Inventor: Jabir Kannathvalappil Moidunny, Kerala (IN)

(73) Assignee: HARMAN INTERNATIONAL INDUSTRIES, INCORPORATED, Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/344,716

(22) Filed: Jun. 29, 2023

(65) Prior Publication Data

US 2023/0347906 A1 Nov. 2, 2023

Related U.S. Application Data

(63) Continuation of application No. 17/455,137, filed on Nov. 16, 2021, now Pat. No. 11,724,703.

(30) Foreign Application Priority Data

Jul. 1, 2021 (IN) .............................. 202141029579

(51) Int. Cl.
G08B 23/00 (2006.01)
B60W 40/08 (2012.01)
(Continued)

(52) U.S. Cl.
CPC ........ *B60W 40/08* (2013.01); *B60W 50/0098* (2013.01); *B60W 50/14* (2013.01);
(Continued)

(58) Field of Classification Search
CPC .. B60W 40/08; B60W 50/0098; B60W 50/14; B60W 2040/0809;
(Continued)

(56) References Cited

U.S. PATENT DOCUMENTS 5,983,147 A 11/1999 Krumm
6,078,854 A 6/2000 Breed et al.
(Continued)

FOREIGN PATENT DOCUMENTS

CN 103796892 B 8/2016
DE 102006032769 A1 1/2008
(Continued)

OTHER PUBLICATIONS

European Patent Office, Extended European Search Report Issued in Application No. 22181150.8, Nov. 29, 2022, Germany, 9 pages.

*Primary Examiner* — Anh V La
(74) *Attorney, Agent, or Firm* — McCoy Russell LLP (57) ABSTRACT

Various systems and methods are provided for determining a posture of an occupant of a vehicle. In one embodiment, a method comprises capturing images of an occupant in a vehicle via a vehicle camera, determining a current posture of the occupant and a recommended posture for the occupant based on the captured images and body measurements of the occupant, and outputting a guidance based on a difference between the current posture and the recommended posture. In this way, a comfort of the occupant may be increased by guiding the occupant toward a more ergonomic posture.

17 Claims, 5 Drawing Sheets

(51) Int. Cl.
  *B60W 50/00* (2006.01)
  *B60W 50/14* (2020.01)
  *G06T 7/50* (2017.01)
  *G06T 7/70* (2017.01)
  *G06V 20/59* (2022.01)
  *G06V 40/10* (2022.01)

(52) U.S. Cl.
  CPC ............... *G06T 7/50* (2017.01); *G06T 7/70* (2017.01); *G06V 20/593* (2022.01); *G06V 40/103* (2022.01); *B60W 2040/0809* (2013.01); *B60W 2040/0872* (2013.01); *B60W 2040/0881* (2013.01); *B60W 2050/143* (2013.01); *B60W 2050/146* (2013.01); *B60W 2540/043* (2020.02); *B60W 2540/221* (2020.02); *B60W 2540/223* (2020.02); *B60W 2540/227* (2020.02); *B60W 2556/10* (2020.02); *G06T 2207/30196* (2013.01); *G06T 2207/30268* (2013.01)

(58) Field of Classification Search
  CPC . B60W 2040/0872; B60W 2040/0881; B60W 2050/143; B60W 2050/146; B60W 2540/043; B60W 2540/221; B60W 2540/223; B60W 2540/227; B60W 2556/10; G06T 7/50; G06T 7/70; G06T 2207/30196; G06T 2207/30268; G06V 20/593; G06V 40/103; G06V 20/597; G06V 40/10; G06V 40/172; A61B 5/107; A61B 5/1116; A61B 5/18; B60N 2/002; B60N 2/0256; B60N 2/0268; B60N 2/0272; B60N 2/0244; B60N 2/22
  USPC .......... 340/573.1, 576, 575, 573.7, 439, 457
  See application file for complete search history.

(56) References Cited

U.S. PATENT DOCUMENTS

| 11,724,703 | B2* | 8/2023 | Moidunny ............ B60W 40/08 340/573.1 |
|---|---|---|---|
| 2011/0080290 | A1* | 4/2011 | Baxi .................... A61B 5/1116 340/573.1 |
| 2015/0366350 | A1 | 12/2015 | Di Censo et al. |
| 2018/0251085 | A1 | 9/2018 | Coburn et al. |
| 2018/0334055 | A1* | 11/2018 | Hennes .................... B60N 2/06 |
| 2019/0347499 | A1* | 11/2019 | Yanagawa ............ G06V 20/597 |
| 2021/0034890 | A1 | 2/2021 | An et al. |
| 2021/0094492 | A1 | 4/2021 | Zender et al. |
| 2021/0150754 | A1 | 5/2021 | Tanaka et al. |
| 2021/0179117 | A1 | 6/2021 | Glazman et al. |
| 2021/0197747 | A1 | 7/2021 | Yoshizawa |

FOREIGN PATENT DOCUMENTS

| DE | 102012223415 | A1 | 6/2014 |
|---|---|---|---|
| DE | 102018122105 | A1 | 3/2020 |
| EP | 2957193 | A1 | 12/2015 |
| WO | 2017164835 | A1 | 9/2017 |
| WO | 2017164847 | A1 | 9/2017 |

* cited by examiner

METHOD AND SYSTEM FOR DRIVER POSTURE MONITORING

CROSS-REFERENCE TO RELATED APPLICATIONS

The present application is a continuation of U.S. Non-Provisional patent application Ser. No. 17/455,137, entitled "METHOD AND SYSTEM FOR DRIVER POSTURE MONITORING", and filed on Nov. 16, 2021. U.S. Non-Provisional patent application Ser. No. 17/455,137 claims priority to Indian Application No. 202141029579, entitled "METHOD AND SYSTEM FOR DRIVER POSTURE MONITORING", and filed on Jul. 1, 2021. The entire contents of the above-listed applications are hereby incorporated by reference for all purposes.

FIELD

The present disclosure relates to a camera-based driver assistance system.

BACKGROUND

Driving posture may affect the health and comfort of an operator of a vehicle. However, it may be difficult for the operator to monitor their own posture while focusing on vehicle operation. As another example, different vehicle occupants, including different operators during different vehicle trips, may have different sizes, including height, weight, and proportions. Therefore, seat settings for one occupant may not facilitate optimal posture for another occupant, and it may be difficult for the occupant to find comfortable and ergonomic seat settings through manual adjustment (e.g., controlled by the occupant). Furthermore, a seat position that is optimal during a vehicle trip may not be optimal for entering or exiting the vehicle for the particular occupant, leading to discomfort or increased physical exertion.

SUMMARY

In various embodiments, the issues described above may be addressed by a method comprising capturing images of an occupant in a vehicle via a vehicle camera, determining a current posture of the occupant and a recommended posture for the occupant based on the captured images and body measurements of the occupant, and outputting a guidance based on a difference between the current posture and the recommended posture. As one example, the body measurements may be received via a user interface, measured via a vehicle sensor, and/or estimated based on the captured images. For example, a surface area and volume of the occupant may be estimated from depth and/or visible light information received from the vehicle camera, and the surface area and volume may be used to estimate a body mass index of the occupant. As another example, determining the current posture of the occupant may include determining a position of a seat in which the occupant is sitting, such as a seat angle, tilt, and longitudinal position, and determining a body position of the occupant relative to the seat, such as a distance from the occupant's head to a headrest of the seat. As a further example, determining the recommended posture may include determining a desired position of the seat and determining a desired body position of the occupant relative to the seat. For example, a computing system may compare the current posture of the occupant to the recommended posture and output the guidance as a message for the occupant to adjust their posture in response to a threshold (or significant) difference between the current posture of the occupant and the recommended posture or a message to maintain their current posture in response to a less than threshold (or insignificant) difference. In this way, a comfort of the occupant may be increased and a physical strain of the occupant may be decreased.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The disclosure may be better understood from reading the following description of non-limiting embodiments, with reference to the attached drawings, wherein below.

DETAILED DESCRIPTION

Figure 3:
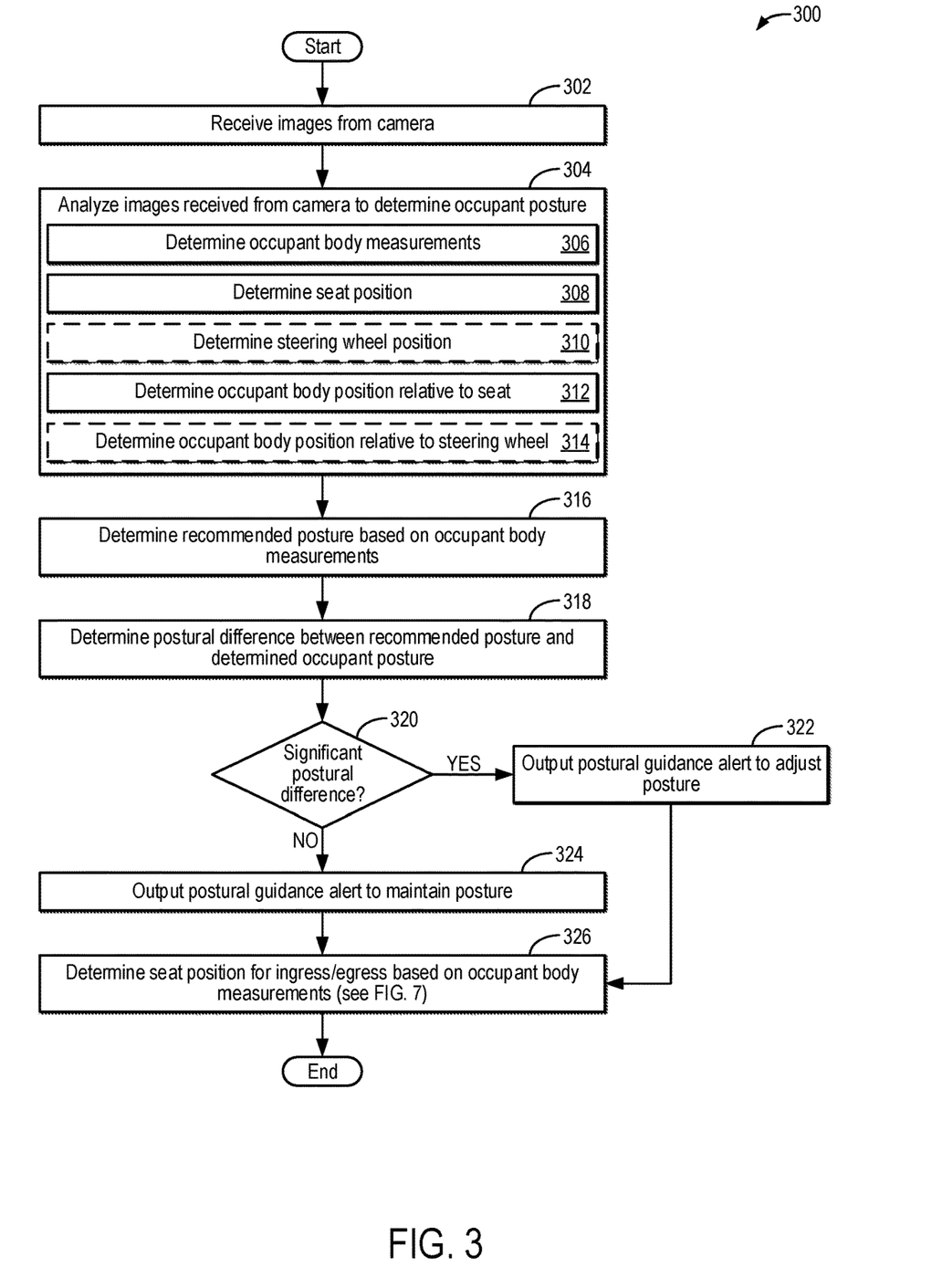
FIG. 3 shows a flow chart of a method for determining occupant posture, according to one or more embodiments.
Figure 4:
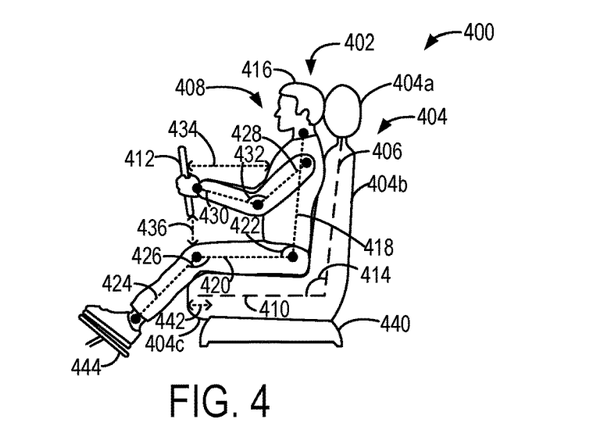
FIG. 4 shows an example of a recommended driving posture, according to one or more embodiments of the present disclosure.
Figure 5:
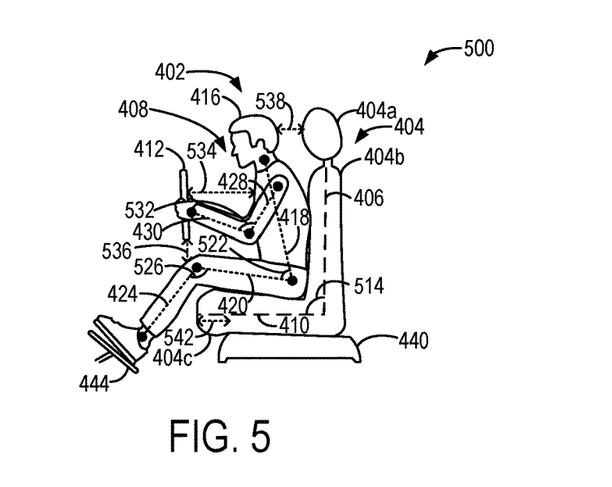
FIG. 5 shows a first example of an incorrect driving posture, according to one or more embodiments of the present disclosure.
Figure 6:
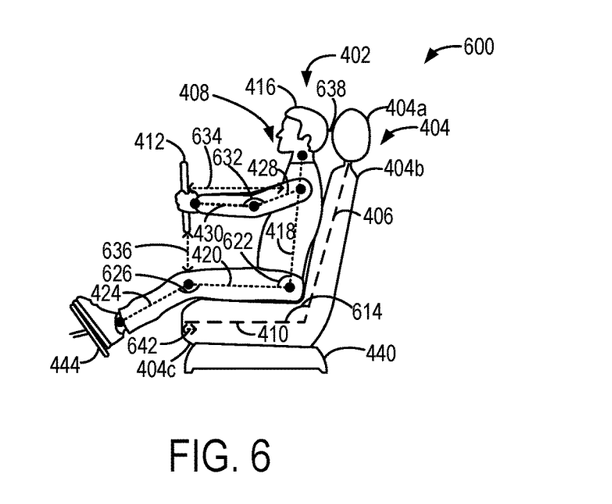
FIG. 6 shows a second example of an incorrect driving posture, according to one or more embodiments of the present disclosure.
Figure 7:
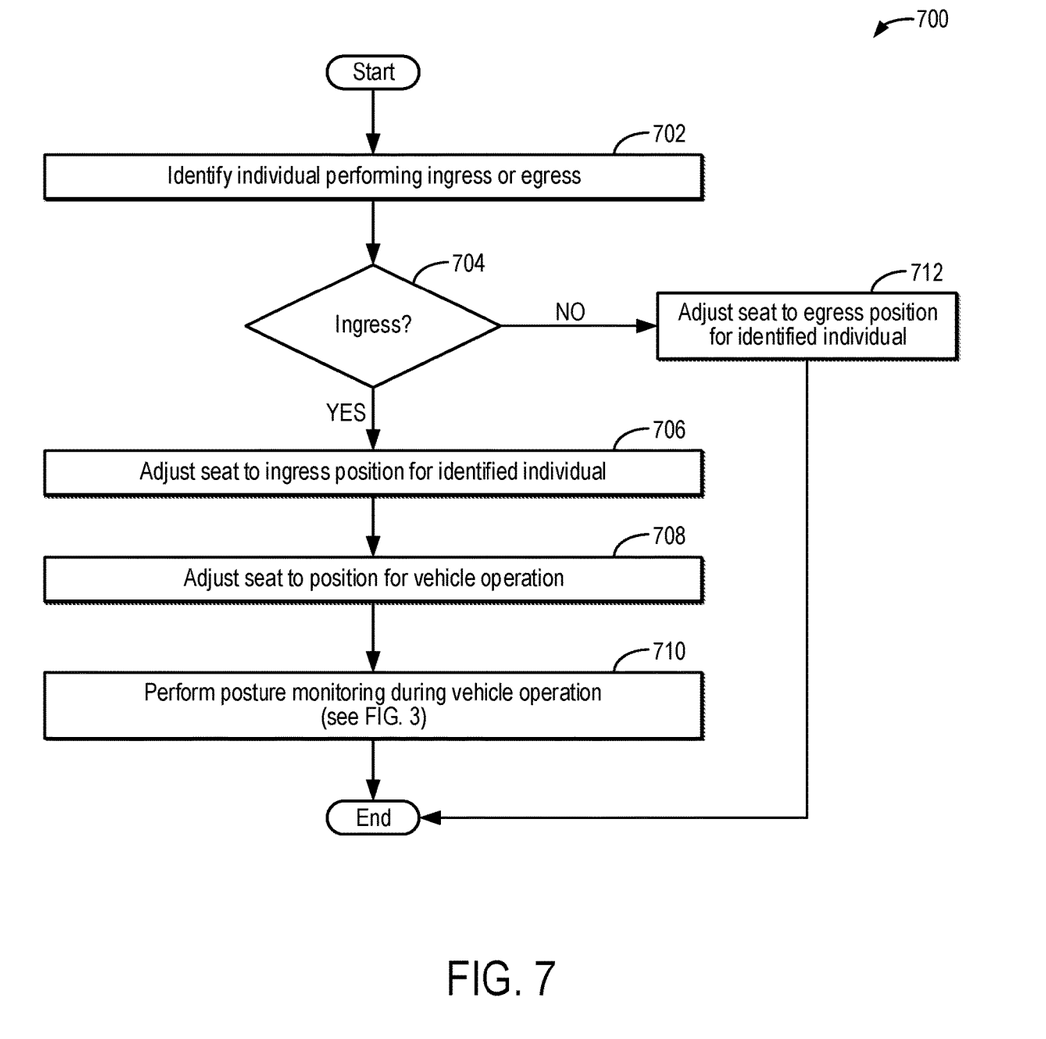
FIG. 7 shows a flow chart of a method for automatically adjusting a seat position during vehicle ingress or egress, according to one or more embodiments.

The following description relates to systems and methods to increase vehicle occupant comfort via a driver monitoring system. The driver monitoring system may include a camera mounted in a vehicle, such as the vehicle shown in FIG. 1. A computing system may process and analyze images received from the camera to determine a posture of the occupant, such as a driver (e.g., operator) or a passenger of the vehicle, and guide posture corrections, such as according to the data flow block diagram shown in FIG. 2. As an example, the computing system may receive images acquired by the camera as well as body measurement data of the occupant. The computing system may use image and data processing resources included in an in-vehicle processing system, a mobile processing system, or a networked processing system (e.g., cloud computing) to identify suitable posture choices, which may be output via a user interface, such as according to the method of FIG. 3. FIGS. 4-6 show various measurements and relationships between the driver, a seat, and a steering wheel that the computing system may analyze in determining the posture of the driver. In particular, an exemplary recommended posture is shown in FIG. 4, while FIGS. 5 and 6 provide examples of incorrect driver posture that may lead to driver discomfort or fatigue. A flow chart of a method for automatically adjusting a seat position to facilitate ingress or egress is shown in FIG. 7, which may use the images and body measurement data analyzed in the method of FIG. 3 to personalize the seat position for each unique vehicle occupant. In this way, driver and passenger comfort may be increased from vehicle entry to vehicle exit and with minimal input from the occupants.

Figure 1:
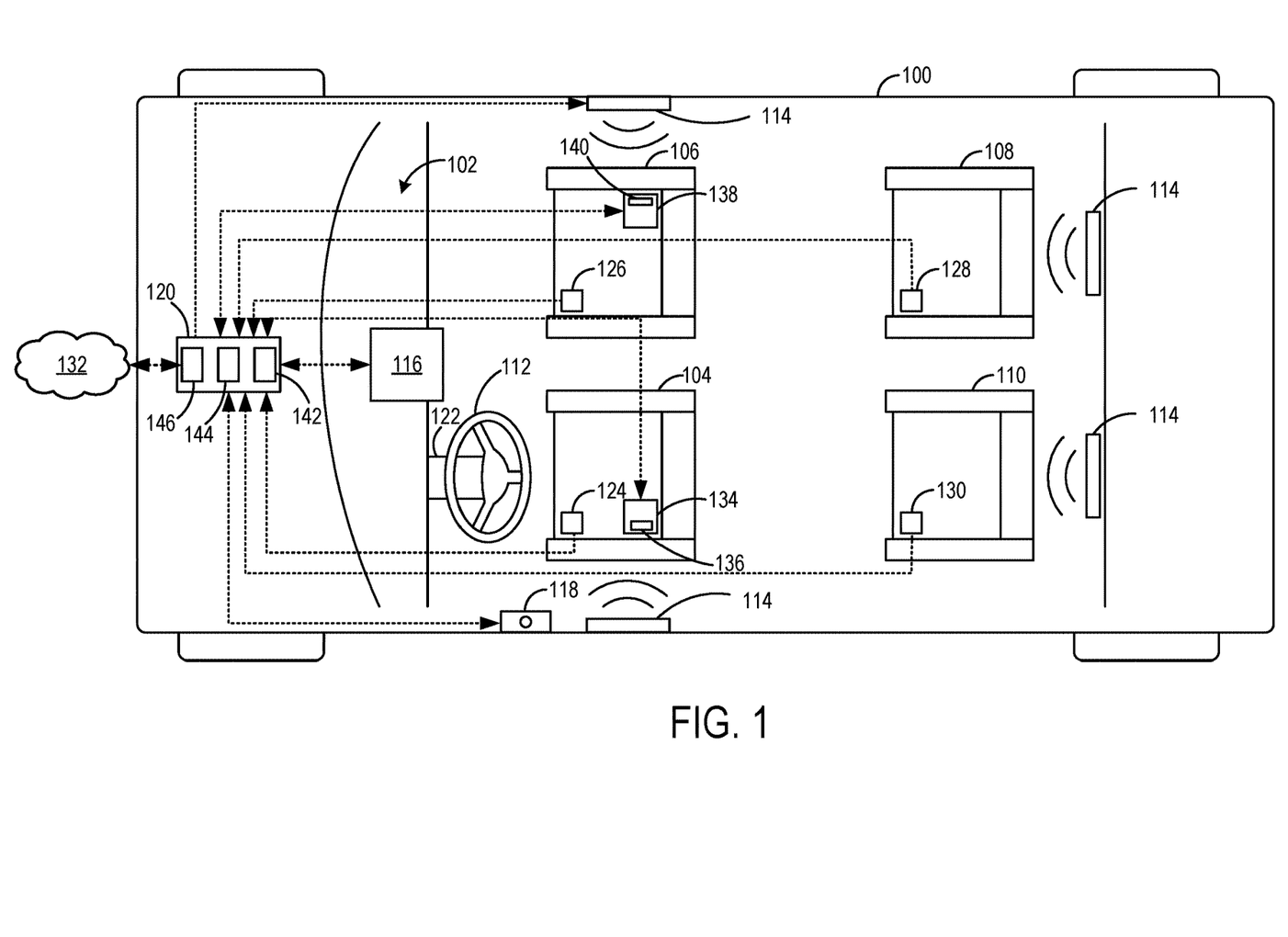
FIG. 1 systematically shows a vehicle system, according to one or more embodiments of the present disclosure.

Turning now to the figures, FIG. 1 schematically shows an exemplary vehicle 100. The vehicle 100 includes a dashboard 102, a driver seat 104, a first passenger seat 106, a second passenger seat 108, and a third passenger seat 110. In other examples, the vehicle 100 may include more or fewer passenger seats. The driver seat 104 and the first passenger seat 106 are located in a front of the vehicle, proximate to the dashboard 102, and therefore may be referred to as front seats. The second passenger seat 108 and the third passenger seat 110 are located at a rear of the vehicle and may be referred to as back (or rear) seats. Additionally, the vehicle 100 includes a plurality of integrated speakers 114, which may be arranged around a periphery of the vehicle 100. In some embodiments, the integrated speakers 114 are electronically coupled to an electronic control system of the vehicle, such as to a computing system 120, via a wired connection. In other embodiments, the integrated speakers 114 may wirelessly communicate with the computing system 120. As an example, an audio file may be selected by an occupant of the vehicle 100, such as a driver passenger, via a user interface 116, and the selected audio file may be projected via the integrated speakers 114. In some examples, audio alerts may be generated by the computing system 120 and also may be projected by the integrated speakers 114, such as will be elaborated herein.

The vehicle 100 further includes a steering wheel 112 and a steering column 122, through which the driver may input steering commands for the vehicle 100. The steering column 122 may be adjustable so that the driver may change a height and/or tilt of the steering wheel 112 by adjusting the steering column 122. In some examples, the steering column 122 may be adjusted by the driver disengaging a lever or lock on the steering column 122 and manually moving the steering column 122 and/or steering wheel 112 to adjust the height and/or tilt of the steering wheel 112. In other examples, the position of the steering column 122 and the steering wheel 112 may be adjusted via an electric motor integrated within the steering column 122. The driver may input adjustments to the electric motor, such as via an interface (e.g., a button or switch) positioned on the steering column 122, or the computing system 120 may actuate the electric motor to adjust the position of the steering column 122 and the steering wheel 112 based on a stored setting for the driver.

The vehicle 100 further includes a camera 118. The camera 118 may be included in a driver monitoring system (e.g., a driver attention monitor). In the embodiment shown in FIG. 1, the camera 118 is positioned to the side of the driver seat 104, which may aid in monitoring the driver in profile. However, in other examples, the camera 118 may be positioned in other locations in the vehicle, such as on the steering column 122 and directly in front of the driver seat 104. The camera 118 may include one or more optical (e.g., visible light) cameras, one or more infrared (IR) cameras, or a combination of optical and IR cameras having one or more view angles. In some examples, the camera 118 may have interior view angles as well as exterior view angles. In some examples, the camera 118 may include more than one lens and more than one image sensor. For example, the camera 118 may include a first lens that directs light to a first, visible light image sensor (e.g., a charge-coupled device or a metal-oxide-semiconductor) and a second lens that directs light to a second, thermal imaging sensor (e.g., a focal plane array), enabling the camera 118 to collect light of different wavelength ranges for producing both visible and thermal images. In some examples, the camera 118 may further include a depth camera and/or sensor, such as a time-of-flight camera or a LiDAR sensor.

In some examples, the camera 118 may be a digital camera configured to acquire a series of images (e.g., frames) at a programmable frequency (e.g., frame rate) and may be electronically and/or communicatively coupled to the computing system 120. Further, the camera 118 may output acquired images to the computing system 120 in real-time so that they may be processed in real-time by the computing system 120 and/or a computer network, as will be elaborated herein with particular respect to FIGS. 2 and 6. As used herein, the term "real-time" denotes a process that occurs instantaneously and without intentional delay. "Real-time" may refer to a response time of less than or equal to about 1 second, for example. In some examples, "real-time" may refer to simultaneous or substantially simultaneous processing, detection, or identification. Further, in some examples, the camera 118 may be calibrated with respect to a world coordinate system (e.g., world space x, y, z).

The vehicle 100 may further include a driver seat sensor 124 coupled to or within the driver seat 104 and a passenger seat sensor 126 coupled to or within the first passenger seat 106. The back seats may also include seat sensors, such as a passenger seat sensor 128 coupled to the second passenger seat 108 and a passenger seat sensor 130 coupled to the third passenger seat 110. The driver seat sensor 124 and the passenger seat sensor 126 may each include one or a plurality of sensors, such as a weight sensor, a pressure sensor, and one or more seat position sensors that output a measurement signal to the computing system 120. For example, the output of the weight sensor or pressure sensor may be used by the computing system 120 to determine whether or not the respective seat is occupied, and if occupied, a weight of a person occupying the seat. As another example, the output of the one or more seat position sensors may be used by the computing system 120 to determine one or more of a seat height, a longitudinal position with respect to the dashboard 102 and the back seats, and an angle (e.g., tilt) of a seat back of the corresponding seat. In other examples, the seat position may be additionally or alternatively determined based on images acquired by the camera 118, such as will be elaborated herein.

In some examples, the vehicle 100 further includes a driver seat motor 134 coupled to or positioned within the driver seat 104 and a passenger seat motor 138 coupled to or positioned within the first passenger seat 106. Although not shown, in some embodiments, the back seats may also include seat motors. The driver seat motor 134 may be used to adjust the seat position, including the seat height, the longitudinal seat position, and the angle of the seat back of the driver seat 104 and may include an adjustment input 136. For example, the adjustment input 136 may include one or more toggles, buttons, and switches. The driver may input desired driver seat position adjustments to the driver seat motor 134 via the adjustment input 136, and the driver seat motor 134 may move the driver seat 104 accordingly in substantially real-time. In other examples, the driver seat motor 134 may adjust the driver seat position based on inputs received from the computing system 120, such as will be described with respect to FIG. 7. The passenger seat motor 138 may adjust a seat position of the passenger seat 106 based on inputs received from an adjustment input 140 and/or based on inputs received from the computing system 120 in an analogous manner. Further, in some examples, the computing system 120 may determine the seat position of the corresponding seat based on feedback from the driver seat motor 134 and the passenger seat motor 138. Although not shown, in some embodiments, the back seats may be adjustable in a similar manner.

The computing system 120 may receive inputs via the user interface 116 as well as output information to the user interface 116. The user interface 116 may be included in a digital cockpit or advanced driver assistance system (ADAS), for example, and may include a display and one or more input devices. The one or more input devices may include one or more touchscreens, knobs, dials, hard buttons, and soft buttons for receiving user input from a vehicle occupant.

The computing system 120 includes a processor 142 configured to execute machine readable instructions stored in a memory 144. The processor 142 may be single core or multi-core, and the programs executed by processor 142 may be configured for parallel or distributed processing. In some embodiments, the processor 142 is a microcontroller. The processor 142 may optionally include individual components that are distributed throughout two or more devices, which may be remotely located and/or configured for coordinated processing. In some embodiments, one or more aspects of the processor 142 may be virtualized and executed by remotely-accessible networked computing devices configured in a cloud computing configuration. For example, the computing system 120 may be communicatively coupled with a wireless network 132 via a transceiver 146, and the computing system 120 may communicate with the networked computing devices via the wireless network 132. Additionally or alternatively, the computing system 120 may directly communicate with the networked computing devices via short-range communication protocols, such as Bluetooth®. In some embodiments, the computing system 120 may include other electronic components capable of carrying out processing functions, such as a digital signal processor, a field-programmable gate array (FPGA), or a graphic board. In some embodiments, the processor 142 may include multiple electronic components capable of carrying out processing functions. For example, the processor 142 may include two or more electronic components selected from a plurality of possible electronic components, including a central processor, a digital signal processor, a field-programmable gate array, and a graphics board. In still further embodiments, the processor 142 may be configured as a graphical processing unit (GPU), including parallel computing architecture and parallel processing capabilities.

Further, the memory 144 may include any non-transitory tangible computer readable medium in which programming instructions are stored. As used herein, the term "tangible computer readable medium" is expressly defined to include any type of computer readable storage. The example methods described herein may be implemented using coded instruction (e.g., computer readable instructions) stored on a non-transitory computer readable medium such as a flash memory, a read-only memory (ROM), a random-access memory (RAM), a cache, or any other storage media in which information is stored for any duration (e.g. for extended period time periods, permanently, brief instances, for temporarily buffering, and/or for caching of the information). Computer memory of computer readable storage mediums as referenced herein may include volatile and non-volatile or removable and non-removable media for a storage of electronically formatted information, such as computer readable program instructions or modules of computer readable program instructions, data, etc. that may be stand-alone or as part of a computing device. Examples of computer memory may include any other medium which can be used to store the desired electronic format of information and which can be accessed by the processor or processors or at least a portion of a computing device. In various embodiments, the memory 144 may include an SD memory card, an internal and/or external hard disk, USB memory device, or a similar modular memory.

Further still, in some examples, the computing system 120 may include a plurality of sub-systems or modules tasks with performing specific functions related to performing image acquisition and analysis. As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations. For example, as will be elaborated herein with respect to FIG. 3, the computing system 120 may determine an occupant posture based on the images received from the camera 118, determine a desired (e.g., recommended) occupant posture based on body measurements, and output an alert in response to the occupant posture not matching the recommended occupant posture.

Figure 2:
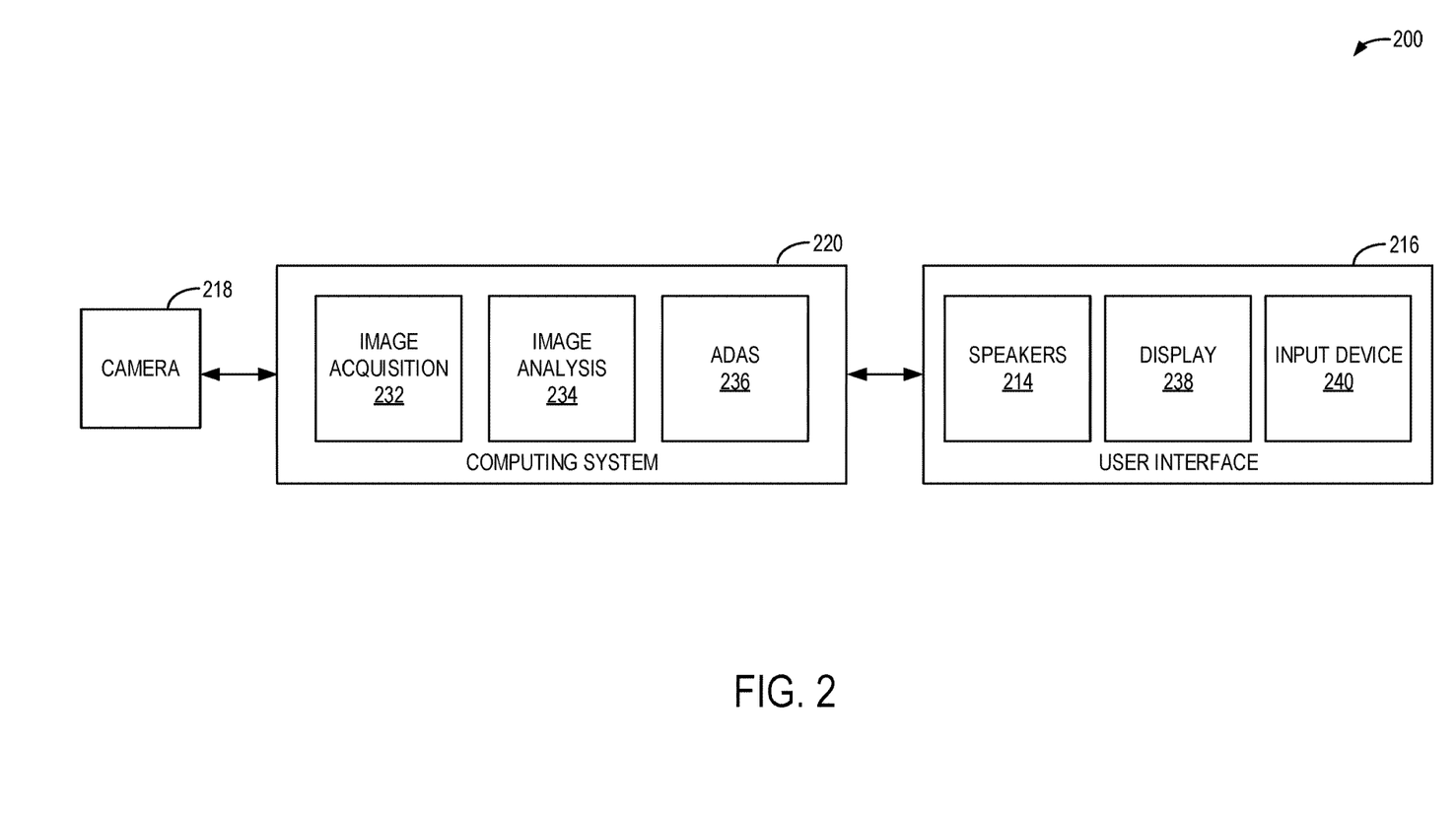
FIG. 2 shows a block diagram of a flow of data during occupant posture detection and recommendation, according to one or more embodiments of the present disclosure.

A data flow between various devices in performing the occupant posture guidance will now be described. Turning to FIG. 2, a block diagram of an example data flow 200 is shown. A camera 218 provides image data to a computing system 220. The camera 218 may be similar to, or the same as, the camera 118 of FIG. 1, and the computing system 220 may be similar to, or the same as, the computing system 120 of FIG. 1. The computing system 220 includes an image acquisition module 232, an image analysis module 234, and an advanced driver assistance system (ADAS) module 236. The image acquisition module 232 may send and receive data with the camera 218. For example, the image acquisition module 232 may control acquisition settings of the camera 218, such as aperture, light sensitivity, focal depth, field of view, shutter speed, frame rate, etc. In some examples, the camera 218 may operate at a frame rate in a range between 4-24 frames per second to substantially continuously capture images of a vehicle interior. In other examples, the frame rate may be lower, such as one frame per second or per multiple seconds (e.g., 30-60 seconds), or higher (e.g., 30 frames per second). As one example, the frame rate may be selected based on a processing speed of the image analysis module 234 so that each image may be fully analyzed before the image analysis module 234 receives a next image in the sequence.

Further, the image acquisition module 232 may update the acquisition settings of the camera 218 based on feedback received from the image analysis module 234. For example, the image analysis module 234 may determine that the images acquired by the camera 218 are too dark and update one or more of the aperture, the light sensitivity, and the shutter speed at the image acquisition module 232 accordingly.

The image analysis module 234 may access images/videos (e.g., an image library) stored in memory and analyze the images received from the camera 218 in real-time to identify one or more features within each of the received image. As one example, the image analysis module 234 may compare a real-time image received from the camera 218 to one stored in memory to identify occupants within the vehicle interior, including a driver and/or a non-driver occupant (e.g., passenger). Additionally or alternatively, the image analysis module 234 may use a computer vision model or algorithm to identify the driver and/or non-driver occupant. In some examples, the image analysis module 234 may further analyze the image, such as using a biometric algorithm that performs facial recognition, to positively identify the occupant(s). As an illustrative example, the biometric algorithm may compare a face of the driver to identification photos of all known drivers of the vehicle to positively identify the driver. Further, the computing system 220 may store user-specific settings and information, including ingress and egress seat settings associated with each known/repeated vehicle occupant, in memory, such as will be elaborated herein with respect to FIGS. 3 and 7.

In some examples, the image analysis module 234 may construct a model of each occupant that includes skeletal tracking. The skeletal tracking may identify various skeletal joints of the occupant (e.g., the driver or the passenger), which may correspond to actual joints of the occupant, centroids of various anatomical structures, terminal ends of the occupant's extremities, and/or points without a direct anatomical link within the occupant (e.g., not corresponding to a particular anatomical structure), and map a simplified virtual skeleton onto the occupant. As each joint of the occupant has at least three degrees of freedom (e.g., world space x, y, z), each joint of the virtual skeleton used for the skeletal tracking may be defined with a three-dimensional (3D) position, and changes in that 3D position may denote movement. In some examples, each joint of the virtual skeleton may also be defined with respect to rotational angle within the 3D world space and with respect to a centerline of the virtual skeleton. In some examples, the image analysis module 234 may use depth and/or visible light information acquired by the camera 218 to define an envelope of the occupant (e.g., the surface area and volume of the occupant), which in turn may be used to approximate a size of the occupant (e.g., a body mass index, height, etc.). As will be elaborated herein and illustrated with respect to FIGS. 4-6, the virtual skeleton may be used to determine limb lengths and joint angles. The limb lengths and joint angles may be used by the image analysis module 234, alone or in combination with the envelope, to determine a 3D posture estimation as well as a recommended (e.g., desired) posture for the particular occupant that will increase comfort and/or health given the size and limb lengths of the individual. Additional details will be described below with respect to FIG. 3.

In some examples, the computing system 220 may receive body measurement inputs from the occupant(s) in addition to or as an alternative to determining the envelope. For example, the ADAS module 236 may prompt the occupant to input height and weight measurements via a user interface 216, which may be similar to, or the same as, the user interface 116 shown in FIG. 1. In particular, the height and weight measurements may be received via an input device 240, and the ADAS module 236 may share the received information with the image analysis module 234. In some examples, the user interface 216 may be included in a smartphone (or tablet, smartwatch, etc.), and the smartphone may run a companion application that interfaces with the ADAS module 236 of the in-vehicle computing system 220 to receive inputs from the occupant and provide alert outputs.

In some examples, the computing system 220 may additionally or alternatively receive occupant weight measurements from seat sensors. For example, a driver seat sensor (e.g., the driver seat sensor 124) may output a driver weight measurement to the computing system 220, and the weight measurement may be used by the image analysis module 234, alone or in combination with the images from the camera 218 and/or the measurements received via the input device 240, to determine body measurements of the driver.

Further, it may be understood that in some examples, the image analysis module 234 may be included in the in-vehicle computing system 220 or accessed via a user-provided mobile computing system, such as a smartphone, computer, or tablet. As another example, the image analysis module 234 may be included via a networked computing system such as a cloud computer or a similar computing environment and accessed remotely (e.g., via a wireless network, such as the wireless network 132 shown in FIG. 0.1). As such, although the image analysis module 234 is shown within the computing system 220 in the example shown in FIG. 2, in other embodiments, at least portions of the image analysis module 234 may be stored in computing devices and/or networks outside of the computing system 220 that are communicatively coupled to the computing system 220.

Once the computing system 220 detects considerable difference between the 3D posture estimation and the recommended posture, the computing system 220 may notify the occupant using the user interface 216. As one example, the ADAS module 236 may interface with the user interface 216 to output an alert via a display 238 and/or speakers 214. The speakers 214 may be in-vehicle speakers, such as the integrated speakers 114 of FIG. 1, or speakers of the smartphone running the companion app. Similarly, the display 238 may be integrated in the vehicle or may be a display of the smartphone running the companion app. For example, the display 238 may output alert messages/symbols, and the speakers 214 may play alert sounds/prompts. The display 238 and/or the speakers 214 may also communicate a recommended sitting posture.

A method for performing the data flow of FIG. 2 will now be described. Turning to FIG. 3, an example method 300 for determining a posture of a vehicle occupant and outputting postural guidance alerts is shown. The method 300 may be executed by a processor of a computing system (e.g., the computing system 120 of FIG. 1 or the computing system 220 of FIG. 2) based on instructions stored on a memory of the computing system (e.g., the memory 144 of FIG. 1). The method 300 will be described with regard to the systems and components of FIGS. 1-2; however, it may be understood that the method may be implemented with other systems and components without departing from the scope of the present disclosure. For clarity, the method 300 will be described with respect to one occupant, which may be a driver or a passenger of the vehicle, although the method 300 may be used to determine the posture of more than one occupant at the same time.

In some examples, the method 300 may be executed in response to a new occupant being detected and/or in response to the occupant adjusting their seat. As another example, additionally or alternatively, the method 300 may be executed at a pre-determined frequency during vehicle operation, such as every 10 minutes, every 30 minutes, every 60 minutes, etc. In some examples, a user may select or adjust the pre-determined frequency. Further, in some examples, the method 300 may be temporarily disabled (e.g., automatically or by the occupant) and/or modified during poor visibility (e.g., fog, heavy rain, snow) or poor road conditions (e.g., slick, icy, or bumpy) while the vehicle is operating at a non-zero speed, as will be elaborated below.

At 302, the method 300 includes receiving images from a camera. As described above with respect to FIG. 1, the camera may include one or more optical, infrared, and depth cameras and may include one or more view angles for capturing images. Further, the camera may capture a sequence of images at a pre-programmed frequency, such as a frequency in a range from 8-24 frames per second. Alternatively, the pre-programmed frequency may be greater than 24 frames per second or less than 8 frames per second. The computing system may receive the images captured by the camera as they are acquired via wired or wireless communication methods, such as Ethernet, USB, Bluetooth®, and WiFi.

At 304, the method 300 includes analyzing the images received from the camera to determine occupant posture. As described above with respect to FIG. 2, the computing system may include an image analysis module (e.g., the image analysis module 234) that analyzes the images received from the camera in real-time to identify one or more features of the occupant in each of the received images. For example, the image analysis module may use one or any combination of an image library, a model, and an algorithm for recognizing the vehicle occupant as well as interior features of the vehicle, such as a seat the occupant is sitting in, a steering wheel, etc. As one example, the computing system may distinguish the driver from one or more additional vehicle occupants based on the location of the driver relative to the steering wheel.

In some embodiments, the computing system may perform facial recognition (e.g., via a biometric algorithm) to determine an identity of the occupant. For example, the identity may include a name or user identification number that is associated with previously received/measured/estimated body measurements, recommended postures, seat settings, or other preferences. When the occupant is unknown, such as when the occupant has not been previously identified, the computing system may create a new user identification number and store images of the occupant for future facial recognition.

Analyzing the images received from the camera to determine occupant posture includes determining occupant body measurements, as indicated at 306. The body measurements may include, but are not limited to, an arm length, a foot length or shoe size, a thigh length, a height, a neck length, and a waist circumference, a weight, and a body mass index (BMI). In some examples, the occupant inputs at least one of the body measurements via a user interface (e.g., the user interface 116 of FIG. 1 or the user interface 216 of FIG. 2). The user interface may be integrated in the vehicle or may be included in a mobile device (e.g., a smartphone, tablet, or smartwatch) that is running a companion application and is in communication with the computing system. For example, the user interface may prompt the occupant to enter and/or update body measurements at a pre-determined frequency (e.g., once a month) or when a new occupant is detected. As another example, additionally or alternatively, the computing system may receive information regarding at least one of the occupant body measurements from an in-vehicle sensor, such as a weight sensor positioned in the seat (e.g., the driver seat sensor 124 of FIG. 1).

Additionally or alternatively, the computing system may estimate at least one of the body measurements based on the received images. For example, depth and/or visible light information acquired by the camera may be used to define a surface area and/or volume of the occupant, which in turn may be used to determine the various body measurements. Further, skeletal tracking may be used to identify joints (e.g., joint angles) and limb lengths. As described above with respect to FIG. 2 and as will be illustrated in FIGS. 4-6, the computing system may model a virtual skeleton of the occupant to determine joint angles and limb lengths.

Analyzing the images received from the camera to determine occupant posture includes determining a seat position, as indicated at 308. The seat position may include, for example, a seat height, a seat angle (e.g., of a seat back relative to a seat cushion), a seat tilt (e.g., of the seat cushion), and a longitudinal seat position. For example, the computing system may identify the seat, including the seat back, the seat cushion, and a headrest, via a computer vision or image recognition algorithm and geometrically analyze the seat back relative to the seat cushion, the seat relative to the dashboard, etc. to determine the seat position. Additionally or alternatively, the computing system may determine the seat position based on an output of a seat position sensor and/or based on feedback from (or a setting of) a seat motor.

When the occupant is the driver, analyzing the images received from the camera to determine occupant posture includes determining a steering wheel position, as optionally indicated at 310. The steering wheel position may include a steering wheel height and tilt angle, for example. The computing system may identify the steering wheel via a computer vision or image recognition algorithm and geometrically analyze the steering wheel relative to the dashboard, relative to a ceiling of the vehicle, relative to a floor of the vehicle, etc. to determine the steering wheel position. Additionally or alternatively, the computing system may determine the steering wheel position based on feedback from (or a setting of) an electronic motor within a steering column that is used to adjust the position of the steering wheel.

Analyzing the images received from the camera to determine occupant posture includes determining the occupant's body position relative to the seat, as indicated at 312. For example, the occupant's body position relative to the seat may include a distance between the occupant's head and the headrest, a distance between the occupant's shoulders relative to the seat back, a distance between the occupant's hips relative to the seat back and seat cushion, and a distance between the occupant's knees and the seat cushion. The distance for each of the above examples may be zero or non-zero. An example where the distance between the occupant's head and the headrest is zero will be described with respect to FIG. 4, while examples where the distance between the occupant's head and the headrest is non-zero will be described with respect to FIGS. 5 and 6. Further, the computing device may estimate the various distances described above according to a real world measurement scale (e.g., inches), a pixel-based scale, or another measurement scale that enables the computing device to compare distances from image to image. For example, the computing system may use an edge detection algorithm to determine a first boundary of the driver's head and a second boundary of the headrest and then determine a number of pixels in a shortest path directly between the first boundary and the second boundary.

When the occupant is the driver, analyzing the images received from the camera to determine occupant posture further includes determining the occupant's body position relative to the steering wheel, as optionally indicated at 314. For example, the occupant's body position relative to the steering wheel may include a clearance distance between the steering wheel and the torso, a clearance between the steering wheel and the thigh, etc. As an example, the computing system may use an edge detection algorithm to determine a first boundary of the steering wheel and a second boundary of the driver's torso and then determine a distance (e.g., in a real-world measurement unit, a number of pixels, or another measurement scale) in a shortest path directly between the first boundary and the second boundary.

At 316, the method 300 includes determining a recommended posture based on the body measurements of the occupant. The computing system may use these body measurements to deduce the recommended sitting posture according to posture recommendations that are stored in memory. For example, the posture recommendations may apply a plurality of body component-specific rules for ergonomic and effective vehicle operation that may be adaptable to a wide variety of body measurements. The posture recommendations may include, but are not limited to, a threshold seat angle range, a threshold clearance distance between the steering wheel and the torso, a threshold clearance between the steering wheel and the thigh, a threshold distance between the head and the headrest, a threshold knee angle range, a threshold hip angle range, a threshold elbow angle range, etc. For example, the computing system may input the body measurements of the occupant into one or more look-up tables or algorithms, which may output the specific posture recommendations for the given body measurements. As one example, the threshold clearance distance between the steering wheel and the torso may be larger for individuals having longer limbs (e.g., longer arms and/or legs) than individuals having shorter limbs. As another example, the threshold distance between the head and the headrest may be the same regardless of body measurements. The look-up table(s) or algorithm(s) may further output a recommended seat position and a recommended steering wheel position that will produce the recommended posture according to the posture recommendations for the given body measurements. Further, in some examples, the posture recommendations may undergo machine learning so that the plurality of body component-specific rules may be updated or refined according to data gathered for the specific occupant or similarly sized occupants.

Further, in some examples, the occupant may input physical limitations that may affect their posture. As one example, the occupant may have a disability or degenerative condition that renders them unable to sit according to the standard body component-specific rules. As such, the computing system may adjust the plurality of body component-specific rules for the given occupant based on the input physical limitations. As an illustrative example, the occupant may have a permanent spinal curvature that may restrict their ability to sit with their shoulders and head back. As such, the occupant may activate accessibility settings and input information regarding a back range of motion.

In some examples, the computing system may further take into account driving conditions, including weather conditions, terrain conditions, a length of time of a current vehicle trip, etc. For example, the plurality of body component-specific rules may be adjusted or relaxed during poor driving conditions so that the occupant, particularly when the occupant is the driver, may have a greater range of movement within the recommended posture. For example, during poor visibility conditions, the driver may instinctively angle their body forward (e.g., toward the steering wheel). As another example, the plurality of body component-specific rules may be less relaxed during a long trip to prevent fatigue.

At 318, the method 300 includes determining a postural difference between the recommended posture and the determined occupant posture. For example, the computing system may compare the actual sitting posture determined from the images from the camera and the recommended posture determined from the body measurements by comparing each specific posture recommendation to the determined posture. That is, the actual seat position may be compared to the recommended seat position, an actual elbow angle of the occupant may be compared to the threshold elbow angle range, etc. In some examples, the computing system may differently weight each posture component (e.g., seat position, steering wheel position, elbow angle, hip angle, various clearance distances) according to its posture contribution. For example, because the seat position may some or all of the various clearance distances and joint angles, the seat position may be more heavily weighted in the comparison, and so smaller differences in the seat position (e.g., one or more of the seat angle, seat height, and longitudinal position) may have a larger impact in determining if the postural difference is significant, as will be described below. As such, the postural difference may include a weighted sum, at least in some examples.

At 320, the method 300 includes determining if the postural difference is significant. A level of significance in the postural difference may be inferred using statistical analysis, such as common thumb rules. In some examples, the computing system may consider the body mass index as an additional factor in the inferencing. For example, an overweight body mass index may adversely affect postural dynamics and hence, even minor postural differences may be considered significant for such persons.

Additionally or alternatively, the method may include determining if the postural difference is greater than or equal to a threshold postural difference, such as by summing or tabulating a magnitude difference or a percentage difference of all of the deviations between the occupant posture and the recommended posture and comparing the sum to the threshold postural difference. The threshold postural difference may be a non-zero magnitude difference or percentage difference that is stored in memory that corresponds to a significant postural difference, for example. As mentioned above, some posture components may be weighted more heavily in the determination.

If the postural difference significant (e.g., statistically significant) or is greater than or equal to the threshold difference, the method 300 proceeds to 322 and includes outputting a postural guidance alert to adjust posture. For example, the user interface may output a visual (e.g., via a display) and/or audible (e.g., via speakers) postural guidance alert to adjust posture. As one example, the postural guidance alert may include a recommendation that the occupant adjust their posture. As another example, the postural guidance alert may include instructions for posture adjustments that are likely to result in the recommend posture. For example, the postural guidance alert may include messages such as "increase set incline" when the seat angle is too far reclined or "position head against headrest" when the distance between the occupant's head and the headrest is greater than the threshold distance. As still another example, additionally or alternatively, the postural guidance alert may include haptic feedback given via the seat or the steering wheel.

If the postural difference is not significant or is less than the threshold difference, the method 300 proceeds to 324 and includes outputting a postural guidance alert to maintain posture. For example, because the occupant posture is determined to be substantially the same as the recommended posture when the postural difference is not significant, the occupant may be encouraged to maintain their current posture. In some examples, the user interface may output a symbol or other message, such as a green check mark next to a posture item on a display or a chime output via the speakers, to inform the occupant that they are sitting in the recommended posture and to maintain their current posture. However, in other examples, the user interface may not output any visual or audible message regarding the occupant posture when the postural difference is not significant, and the message to maintain posture may be implied based on the absence of posture changing guidance.

At 326, the method 300 includes determining a seat position for ingress (e.g., entering the vehicle) and a seat position for egress (e.g., exiting the vehicle) based on the body measurements of the occupant. For example, it may be desirable to change the seat angle, the seat tilt, and the seat longitudinal position to make it easier to enter or exit the vehicle. As one example, the longitudinal position may be further back for an occupant with a longer leg length and/or larger BMI compared with the longitudinal position for an occupant with a shorter leg length and/or smaller BMI. In some examples, the seat position for ingress is the same as the seat position for egress, while in other examples, the seat positions may be different for ingress and egress. The determined seat position for ingress and the determined seat position for egress may be stored in the memory of the computing system for recall during ingress/egress, as will be elaborated below with respect to FIG. 7. The method 300 may then end.

Exemplary parameters or components that may be used by a computing system (e.g., the computing system 120 of FIG. 1 or the computing system 220 of FIG. 2) in determining a driver posture will now be described with reference to FIGS. 4-6. Features of FIGS. 4-6 that are the same throughout the different driver postures are numbered the same and will not be reintroduced between figures, while parameters (e.g., angles and distances) that change between the different driver postures are numbered differently, as will be elaborated below. For example, each of FIGS. 4-6 illustrates a side view of a driver 402 sitting in a driver seat 404, which may be the driver seat 104 of FIG. 1, for example. The driver seat 404 includes a headrest 404a, a seat back 404b, and a seat cushion 404c. The seat back 404b has a length 406, and the seat cushion 404c has a length 410. Further, the driver seat 404 is coupled to a floor of the vehicle (not shown) via a seat base 440. The seat base 440 is fixedly coupled (e.g., bolted) to the floor of the vehicle and does not move with respect to the floor of the vehicle. However, the driver seat 404 may move relative to the seat base. For example, a vertical position (e.g., seat height) and a longitudinal position (e.g., how forward or back the seat is with respect to the front and back of the vehicle) of the driver seat 404 may be adjusted with respect to the seat base 440. Each of FIGS. 4-6 further includes a steering wheel 412, which may be the steering wheel 112 of FIG. 1, for example, and a pedal 444, which may represent an accelerator pedal, a brake pedal, or a clutch.

A virtual skeleton 408 is mapped onto (e.g., overlaid on) the driver 402 and includes nodes representing joints and dashed lines representing the general connectivity of the joints. In the example shown, the virtual skeleton 408 maps ankle, knee, hip, wrist, elbow, shoulder, and neck joints. The virtual skeleton 408 may be used by the computing system to aid in determining the driver posture, such as described above with respect to FIGS. 2 and 3. For example, the virtual skeleton 408, and thus the driver 402, has a torso length 418 extending between the neck joint and a midpoint between hip joints (e.g., at a pelvis), an upper leg (e.g., thigh) length 420 extending between the hip joint and the knee joint, a lower leg (e.g., shin) length 424 extending between the ankle joint and the knee joint, an upper arm length 428 extending between the shoulder joint and the elbow joint, and a lower arm length 430 extending between the elbow joint and the wrist joint. Although not shown in FIGS. 4-6, other body measurements may also be estimated, such as an angle of a head 416 of the driver 402, a foot length and angle, etc. As such, FIGS. 4-6 are meant to illustrate non-limiting examples of different body measurements that may be obtained according to the systems and methods described herein and illustrate one exemplary embodiment of postural mapping using a virtual skeleton.

Referring now to FIG. 4, a first posture 400 is shown. The first posture 400 is one example of a recommended driving posture that follows posture recommendations for ergonomic and effective vehicle operation, such as described with respect to FIG. 3. In the first posture 400, the driver seat 404 is positioned at a seat angle 414, and the head 416 is in contact with the headrest 404a such that there is no distance (e.g., space) between the head 416 and the headrest 404a. For example, the seat angle 414 may be within a threshold range for driver comfort and vision. The threshold range may extend from 93 to 100 degrees and may vary based on the body measurements of the driver 402. For example, the threshold range may be between 94 and 99 degrees for a first driver, between 93 and 101 degrees for a second driver, and between 94 and 97 degrees for a third driver. The threshold range may help ensure that the driver 402 is not so reclined that vehicle operation is obstructed and not so inclined that comfort is reduced.

The first posture 400 further includes a first clearance distance 434 between the steering wheel 412 and the torso of the driver 402, a second clearance distance 436 between the steering wheel 412 and the thigh of the driver 402, and a longitudinal seat position represented by a distance 442 between a forward-most upper corner of the seat base 440 (with respect to the vehicle) and a forward-most edge of the seat cushion 404c. However, the computing system may use other references in determining the longitudinal seat position. Although not shown in the present example, a seat height may also be determined.

The first posture 400 further includes a knee angle 426, a hip angle 422, and an elbow angle 432. The knee angle 426 is formed at the knee joint between the lower leg length 424 and the upper leg length 420, the hip angle is formed at the hip joint between the upper leg length 420 and the torso length 418, and the elbow angle 432 is formed at the elbow joint between the lower arm length 430 and the upper arm length 428. Note that although FIG. 4 is a two-dimensional illustration of a 3D scene, the knee angle 426, the hip angle 422, and the elbow angle 432 may be defined in three dimensions (e.g., using x, y, and z world coordinates).

Due to the longitudinal seat position represented by the distance 442 and the seat angle 414, the first clearance distance 434 and the second clearance distance 436 provide sufficient room for the driver to maneuver without contacting the steering wheel 412. Further, the knee angle 426 allows the driver to fully depress the pedal 444 without fully unbending the knee joint. Further, because the driver's arms are bent at the obtuse elbow angle 432, the driver may easily reach the steering wheel 412.

Referring now to FIG. 5, a second posture 500 is shown. The second posture 500 is a first example of an incorrect driving posture that may cause driver strain and/or degrade the driver's ability to operate the vehicle. In the second posture 500, the driver seat 404 is positioned at a seat angle 514 and has a longitudinal position with a distance 542 between the forward-most upper corner of the seat base 440 and a forward-most edge of the seat cushion 404c. The seat angle 514 is less than the seat angle 414 of the first posture 400 of FIG. 4 and is outside of the threshold range for driver comfort and vision. For example, the seat angle 514 may be approximately 90 degrees, causing the seat back 404b to be so vertically upright that the driver 402 hunches forward toward the steering wheel 412. As a result, a hip angle 522 of the driver 402 in the second posture 500 is also less than the hip angle 422 of the first posture 400 of FIG. 4. The distance 542 of the second posture 500 is greater than the distance 442 of the first posture 400. Thus, the longitudinal position of the seat 404 is further forward in the second posture 500 than in the first posture 400 of FIG. 4. As a result of both the further forward longitudinal position and the smaller seat angle 514, both a first clearance distance 534 between the steering wheel 412 and the torso of the driver 402 and the second clearance distance 536 between the steering wheel 412 and the knee of the driver 402 are less than the first clearance distance 434 and the second clearance distance 436 of FIG. 4, respectively. As a result of the smaller second clearance distance 536, the driver 402 may be more likely to contact the steering wheel 412 with a knee. Further, the head 416 is a distance 538 from the headrest 404a. As a result, the driver 402 may expend additional energy and experience muscle fatigue by leaning forward instead of resting the head 416 against the headrest 404a and may be closer to the steering wheel 412 than desired for vehicle operation.

The second posture 500 further includes a knee angle 526 and an elbow angle 532. Because the first clearance distance 534 in the second posture 500 is smaller than the first clearance distance 434 in the first posture 400, the elbow angle 532 is smaller (e.g., more acute) than the elbow angle 432 of the first posture 400 of FIG. 4. Similarly, the knee angle 526 is smaller (e.g., more acute) than the knee angle 426 of the first posture 400 of FIG. 4. Overall, the driver 402 is positioned inefficiently and in a manner that may cause strain and/or fatigue, making the second posture 500 undesirable. The computing system may provide feedback accordingly so that the driver may adjust from the second posture 500 to the first posture 400, such as according to the method of FIG. 3. For example, the computing system may recommend increasing the seat angle 514, decreasing the distance 542, resting the head 416 on the headrest 404a, etc.

Continuing to FIG. 6, a third posture 600 is shown. The third posture 600 is a second example of an incorrect driving posture that may cause driver strain and/or degrade the driver's ability to operate the vehicle. In the third posture 600, the driver seat 404 is positioned at a seat angle 614 and has a longitudinal position with a distance 642 between the forward-most upper corner of the seat base 440 and a forward-most edge of the seat cushion 404c. The seat angle 614 is greater than the seat angle 414 of the first posture 400 of FIG. 4 and is outside of the threshold range for driver comfort and vision. For example, the seat angle 614 may be approximately 105 degrees, causing the seat back 404b to be further reclined than desired. Further, the distance 642 of the third posture 600 is less than the distance 442 of the first posture 400. Thus, the longitudinal position of the seat 404 is further backward in the third posture 600 than in the first posture 400 of FIG. 4. As a result of both the further backward longitudinal position and the larger seat angle 614, both a first clearance distance 634 between the steering wheel 412 and the torso of the driver 402 and the second clearance distance 636 between the steering wheel 412 and the knee of the driver 402 are greater than the first clearance distance 434 and the second clearance distance 436 of FIG. 4, respectively. In particular, the larger first clearance distance 634 is such that the arms of the driver 402 are nearly fully extended to reach the steering wheel 412. As a result, an elbow angle 632 is greater than the elbow angle 432 of the first posture 400 and nears 180 degrees.

Further, a hip angle 622 of the driver 402 in the third posture 600 is greater than the hip angle 422 of the first posture 400 of FIG. 4 due to the greater seat angle 614 (e.g., the seat is more reclined). As another example, the head 416 has a distance 638 from the headrest 404a. Even though the distance 638 is less than the distance 538 of the second position of FIG. 5, the driver 402 still may expend additional energy and experience muscle fatigue by not resting the head 416 against the headrest 404a.

The third posture 600 further includes a knee angle 626. Because the longitudinal seat position is further back than in the first posture 400, the knee angle 626 is greater (e.g., more obtuse) than the knee angle 426 in the first posture 400. For example, the knee angle 626 is such that the leg is approaching a fully extended position. As a result, the driver 402 may be unable to fully depress the pedal 444 without sliding forward in the seat 404, away from the seat back 404b. Overall, the driver 402 is positioned inefficiently and in a manner that may cause strain and/or fatigue due to the seat angle 614 being outside of the threshold range, making the third posture 600 undesirable. The computing system may provide feedback accordingly so that the driver may adjust from the third posture 600 to the first posture 400, such as according to the method of FIG. 3. For example, the computing system may recommend decreasing the seat angle 614, increasing the distance 642, resting the head 416 on the headrest 404a, etc.

Turning now to FIG. 7, an example method 700 is shown for adjusting a seat position during vehicle ingress or egress. The method 700 may be executed by a processor of a computing system (e.g., the computing system 120 of FIG. 1 or the computing system 220 of FIG. 2) based on instructions stored on a memory of the computing system (e.g., the memory 144 of FIG. 1). The method 700 will be described with regard to the systems and components of FIGS. 1-2; however, it may be understood that the method may be implemented with other systems and components without departing from the scope of the present disclosure. For clarity, the method 700 will be described with respect to one vehicle seat, which may be a driver seat or a passenger seat of the vehicle, although the method 700 may be used to adjust more than one seat at the same time. Further, the method 700 may be executed whenever vehicle ingress or egress is indicated, such as will be elaborated below.

At 702, the method 700 includes identifying an individual performing ingress or egress. In some examples, the computing system may identify the individual performing ingress or egress based on a unique identity of a key fob or smart key carried by the individual, a biometric parameter used by the individual for vehicle unlock (e.g., thumbprint, facial recognition, etc.), and/or a signal received from a mobile device carried by the individual (e.g., a smartphone, tablet, or smartwatch). As another example, the computing system may receive images from a camera (e.g., the camera 118 of FIG. 1 or the camera 218 of FIG. 2) and perform facial recognition to identify the individual, such as described with respect to FIG. 3. If the individual is not currently known to the computing system, the computing system may assign a new user identification number and store images of the individual for future facial recognition, at least in some examples.

At 704, the method 700 includes determining if the individual is performing ingress. For example, the individual may be performing ingress when the individual is outside of the vehicle, when the vehicle is unlocked while being at rest, in response to a door being opened while being at rest, in response to a remote start, and so forth. As such, the vehicle being unlocked while at rest, the door being opened while the vehicle is at rest, the remote start, detecting a proximity of a key fob, etc. all provide indications of ingress. In contrast, the individual may not be performing ingress, and may thus be performing egress, when the individual is already inside of the vehicle, in response to the vehicle being shut down, in response to an ignition key being removed, etc. As such, the occupant being inside the vehicle at the time of vehicle shutdown and the ignition key being removed provide indications of egress.

If the individual is performing ingress, the method 700 proceeds to 706 and includes adjusting the seat to an ingress position for the identified individual. If the individual is not known and body measurement information is not known, a default ingress position may be used. Otherwise, when the individual is known and/or the computing system has body measurement information, the computing system may determine the ingress position, such described with respect to the method of FIG. 3. The ingress position may include settings for a seat tilt, a seat angle, a seat height, and a seat longitudinal position. The computing system may adjust the seat tilt, the seat angle, the seat height, and/or the seat longitudinal position to the ingress position via a seat motor.

At 708, the method 700 includes adjusting the seat to a position for vehicle operation. For example, the computing system may further adjust the seat position from the ingress position after the individual enters the vehicle and is positioned within the seat and before the vehicle starts moving. In some examples, the position for vehicle operation may be the most recently used seat settings for the identified individual that are stored in memory. If the individual is not known and body measurement information is not known, a default seat position may be used. In some examples, the computing system may determine the seat position based on body measurements of the individual, when available, such described with respect to the method of FIG. 3. The seat position for vehicle operation may include settings for the seat tilt, the seat angle, the seat height, and the seat longitudinal position that are expected to be comfortable and ergonomic for the given individual. Further, some or all of the settings for the seat position for vehicle operation may be different than the seat settings for ingress. As such, the computing system may adjust the seat tilt, the seat angle, the seat height, and the seat longitudinal position to the seat position for the vehicle operation via the seat motor.

At 710, the method 700 includes performing posture monitoring during vehicle operation, such as according to the method of FIG. 3. In this way, a likelihood that the individual remains in a comfortable and ergonomic position during vehicle operation is increased. The method 700 may then end.

Returning to 704, if the individual is not performing ingress (e.g., the individual is performing egress), the method 700 proceeds to 712 and includes adjusting the seat to an egress position for the identified individual. If the individual is not known and body measurement information is not known, a default egress position may be used. Otherwise, when the individual is known and/or the computing system has body measurement information, the computing system may determine the egress position, such described with respect to the method of FIG. 3. The egress position may include settings for the seat tilt, the seat angle, the seat height, and the seat longitudinal position, any or all of which may be the same as or different from the seat settings for ingress as well as the seat settings for vehicle operation. The computing system may adjust the seat tilt, the seat angle, the seat height, and/or the seat longitudinal position to the egress position via the seat motor. Thus, the individual may be able to comfortably exit the vehicle, and the method 700 may end.

In this way, a comfort of an occupant of a vehicle, such as a driver or a non-driver passenger, may be increased while entering the vehicle, while the vehicle is in operation, and while exiting the vehicle. Further, because posture monitoring is automated by a computing system, the driver may focus on operating the vehicle instead of monitoring their own posture. Further still, an amount of time it takes for the driver to achieve an ergonomic and effective driving posture may be reduced using the posture guidance. For example, the driver may not spend time trying out different seat adjustments and steering wheel adjustments to see what feels more comfortable but may instead allow the computing system to determine optimal settings for their body measurements. As such, the driver may follow adjustment prompts to achieve the optimal settings.

The technical effect of monitoring a sitting posture of a vehicle occupant and providing feedback in response to the sitting posture being significantly different from a recommended posture is that a comfort of the vehicle occupant may be increased.

The disclosure also provides support for a method, comprising: capturing images of an occupant in a vehicle via a vehicle camera, determining a current posture of the occupant and a recommended posture for the occupant based on the captured images and body measurements of the occupant, and outputting a guidance based on a difference between the current posture and the recommended posture. In a first example of the method, at least one of the body measurements is received via a user interface. In a second example of the method, optionally including the first example, at least one of the body measurements is measured via a sensor of the vehicle. In a third example of the method, optionally including one or both of the first and second examples, the method further comprises: estimating at least one of the body measurements based on the captured images. In a fourth example of the method, optionally including one or more or each of the first through third examples, estimating the at least one of the body measurements based on the captured images comprises determining a surface area and volume of the occupant using at least one of depth and visible light information from the captured images. In a fifth example of the method, optionally including one or more or each of the first through fourth examples, the occupant is sitting in a seat, and determining the current posture of the occupant comprises: determining a seat position of the seat, and determining a body position of the occupant relative to the seat. In a sixth example of the method, optionally including one or more or each of the first through fifth examples, the seat position of the seat includes an angle of a seat back of the seat, a tilt of a seat cushion of the seat, and a longitudinal position of the seat within the vehicle, the body position of the occupant relative to the seat includes a distance from a head of the occupant to a headrest of the seat, and determining the recommended posture for the occupant comprises determining a desired angle of the seat back, a desired tilt of the seat cushion, a desired longitudinal position of the seat within the vehicle, and a desired distance from the head of the occupant to the headrest of the seat based on the body measurements of the occupant and a plurality of body component-specific posture rules. In a seventh example of the method, optionally including one or more or each of the first through sixth examples, outputting the guidance based on the difference between the current posture and the recommended posture comprises: determining a first difference between the angle of the seat back of the seat and the desired angle of the seat back of the seat, a second difference between the tilt of the seat cushion of the seat and the desired tilt of the seat cushion, a third difference between the longitudinal position of the seat within the vehicle and the desired longitudinal position of the seat within the vehicle, and a fourth difference between the distance from the head of the occupant to the headrest of the seat and the desired distance, outputting the guidance to adjust posture in response to a weighted sum of the first difference, the second difference, the third difference, and the fourth difference being greater than or equal to a threshold difference, and outputting the guidance to maintain posture in response to the weighted sum being less than the threshold difference. In an eighth example of the method, optionally including one or more or each of the first through seventh examples, the occupant is a driver of the vehicle, and determining the current posture of the occupant further comprises: determining a position of a steering wheel, and determining the body position of the occupant relative to the steering wheel. In a ninth example of the method, optionally including one or more or each of the first through eighth examples, the position of the steering wheel includes a height of the steering wheel and a tilt of the steering wheel, the body position of the occupant relative to the steering wheel includes a first clearance distance between the steering wheel and a torso of the occupant and a second clearance distance between the steering wheel and a thigh of the occupant, and determining the recommended posture for the occupant comprises determining a desired height of the steering wheel, a desired tilt of the steering wheel, a desired first clearance distance, and a desired second clearance distance based on the body measurements of the occupant and a plurality of body component-specific posture rules. In a tenth example of the method, optionally including one or more or each of the first through ninth examples, outputting the guidance based on the difference between the current posture and the recommended posture comprises: determining a first difference between the height of the steering wheel and the desired height of the steering wheel, a second difference between the tilt of the steering wheel and the desired tilt of the steering wheel, a third difference between the first clearance distance and the desired first clearance distance, and a fourth difference between the second clearance distance and the desired second clearance distance, and outputting the guidance as a visual and/or audible alert in response to a weighted sum of the first difference, the second difference, the third difference, and the fourth difference being greater than a threshold difference.

The disclosure also provides support for a method, comprising: receiving image data from a camera of a vehicle, providing feedback for a posture of an occupant in a seat of the vehicle based on the image data received from the camera and body measurements of the occupant, and adjusting a position of the seat for an ingress and an egress of the occupant based on the image data received from the camera and the body measurements of the occupant. In a first example of the method, providing the feedback for the posture of the occupant of the vehicle based on the image data received from the camera and body measurements of the occupant comprises: analyzing the image data received from the camera to determine a current position of the seat, a current position of the occupant relative to the seat, and the body measurements of the occupant, determining a desired position for the seat and a desired position of the occupant relative to the seat by applying the body measurements of the occupant to a plurality of body component-specific posture recommendations, and outputting a postural guidance alert in response to a statistically significant difference between the current position of the seat and the desired position for the seat or the current position of the occupant relative to the seat and the desired position of the occupant relative to the seat. In a second example of the method, optionally including the first example, adjusting the position of the seat for the ingress and the egress of the occupant based on the image data received from the camera comprises: determining a first position of the seat for the ingress of the occupant and a second position of the seat for the egress of the occupant based on the body measurements of the occupant, adjusting the seat to the first position in response to an indication of the ingress of the occupant, and adjusting the seat to the second position in response to an indication of the egress of the occupant. In a third example of the method, optionally including one or both of the first and second examples, adjusting the position of the seat for the ingress and the egress of the occupant based on the image data received from the camera comprises: identifying the occupant by inputting the image data received from the camera into a biometric algorithm, receiving a stored seat position for the ingress and the egress associated with the identified occupant, and actuating a seat motor to adjust the position of the seat to the stored seat position for the ingress and the egress in response to an indication of the ingress or the egress.

The disclosure also provides support for a system for a vehicle, comprising: a camera, and a computing system including instructions stored in non-transitory memory that, when executed, cause the computing system to: receive images captured of an occupant in the vehicle from the camera, determine body measurements of the occupant from the received images, determine a current posture of the occupant from the received images, determine a recommended posture for the occupant based on the determined body measurements, and output an alert responsive to a difference between the current posture and the recommended posture exceeding a threshold difference. In a first example of the system, the occupant is positioned in a seat of the vehicle, and wherein to determine the current posture of the occupant from the received images, the computing system includes further instructions stored in the non-transitory memory that, when executed, cause the computing system to: determine a plurality of posture components of the occupant from the received images, the plurality of posture components including an angle of each joint of the occupant, a position of the occupant relative to the seat of the vehicle, and seat position settings of the seat. In a second example of the system, optionally including the first example, to determine the recommended posture for the occupant based on the determined body measurements, the computing system includes further instructions stored in the non-transitory memory that, when executed, cause the computing system to: determine a plurality of recommended posture components for the occupant based on the body measurements and a plurality of body component-specific posture recommendations, the plurality of recommended posture components including a recommended angle of each joint, a recommended position of the occupant relative to the seat, and recommended seat position settings. In a third example of the system, optionally including one or both of the first and second examples, to output the alert responsive to the difference between the current posture and the recommended posture exceeding the threshold difference, the computing system includes further instructions stored in the non-transitory memory that, when executed, cause the computing system to: determine differences between each of the plurality of posture components of the occupant and each of the corresponding plurality of recommended posture components, and output the alert responsive to a sum of the differences exceeding the threshold difference. In a fourth example of the system, optionally including one or more or each of the first through third examples, the alert includes instructions for achieving the recommended posture, including instructions for achieving the recommended seat position settings and the recommended position of the occupant relative to the seat.

The description of embodiments has been presented for purposes of illustration and description. Suitable modifications and variations to the embodiments may be performed in light of the above description or may be acquired from practicing the methods. For example, unless otherwise noted, one or more of the described methods may be performed by a suitable device and/or combination of devices, such as the embodiments described above with respect to FIGS. 1-2. The methods may be performed by executing stored instructions with one or more logic devices (e.g., processors) in combination with one or more hardware elements, such as storage devices, memory, hardware network interfaces/antennas, switches, clock circuits, and so on. The described methods and associated actions may also be performed in various orders in addition to the order described in this application, in parallel, and/or simultaneously. The described systems are exemplary in nature, and may include additional elements and/or omit elements. The subject matter of the present disclosure includes all novel and non-obvious combinations and sub-combinations of the various systems and configurations, and other features, functions, and/or properties disclosed.

As used in this application, an element or step recited in the singular and preceded with the word "a" or "an" should be understood as not excluding plural of said elements or steps, unless such exclusion is stated. Furthermore, references to "one embodiment" or "one example" of the present disclosure are not intended to be interpreted as excluding the existence of additional embodiments that also incorporate the recited features. The terms "first," "second," "third," and so on are used merely as labels and are not intended to impose numerical requirements or a particular positional order on their objects unless explicitly stated to the contrary.

The following claims particularly point out subject matter from the above disclosure that is regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method, comprising:
    capturing images of a driver of a vehicle via a vehicle camera;
    determining a current posture of the driver based on the captured images based on a relative position of the driver's body to a seat and a relative position of the driver's body to a steering wheel;
    determining a recommended posture for the driver based on the captured images; and
    determining a difference between the current posture and the recommended posture and determining if the difference is significant,
    wherein determining the current posture of the driver includes determining a height of the steering wheel, a tilt of the steering wheel, a first clearance distance between the steering wheel and a torso of the driver, and a second clearance distance between the steering wheel and a thigh of the driver.

2. The method of claim 1, wherein determining the current posture of the driver includes using edge detection to determine a distance between the driver's body and the seat and a distance between the driver's body and the steering wheel.

3. The method of claim 1, wherein determining the recommended posture for the driver includes determining a desired height of the steering wheel, a desired tilt of the steering wheel, a desired first clearance distance between the steering wheel and a torso of the driver, and a desired second clearance distance between the steering wheel and a thigh of the driver, and the recommended posture is further based body measurements of the driver.

4. The method of claim 1, wherein determining if the difference is significant utilizes a weight sum of a plurality of deviations between the current posture and the recommended posture.

5. The method of claim 1, wherein determining a difference between the current posture and the recommended posture includes comparing a recommended elbow angle and a current elbow angle and comparing a recommended distance between the driver's head and the headrest and a current distance between the driver's head and the headrest.

6. A method, comprising:
    receiving image data from a camera of a vehicle;

providing feedback for a posture of an occupant in a seat of the vehicle based on the image data received from the camera and body measurements determined from the image data;

analyzing the image data received from the camera to determine a current position of the seat, position of a steering wheel, position of the occupant relative to the seat, and position of the occupant relative to the steering wheel; and determining a desired position for the seat, a desired position of the occupant relative to the seat, and desired position of the occupant relative to the steering wheel by applying the body measurements of the occupant to a plurality of body component-specific posture recommendations, wherein the desired position of the occupant relative to the steering wheel comprises:

a difference between a first clearance of the steering wheel and a torso of the occupant and the desired first clearance, and a second difference between a second clearance of the steering wheel and a thigh of the occupant and the desired second clearance.

7. The method of claim 6, further comprising adjusting a position of the seat for an ingress and an egress of the occupant based on the image data received from the camera and the body measurements of the occupant, including:

determining a first position of the seat for the ingress of the occupant and a second position of the seat for the egress of the occupant, based on the body measurements of the occupant.

8. The method of claim 6, wherein body measurements determined from the image data are based on a surface area and volume of the occupant using at least one of depth and visible light information from the captured images.

9. The method of claim 6, wherein current position of the occupant relative to the seat includes a distance from a head of the occupant to a headrest of the seat; and determining the desired position of the occupant relative to the seat comprises determining a desired distance from the head of the occupant to the headrest of the seat based on the body measurements of the occupant and a plurality of body component-specific posture rules.

10. The method of claim 6, wherein a postural guidance alert is generated in response to the first difference or second distance being statistically significant.

11. The method of claim 6, wherein the desired position of the occupant relative to the steering wheel further comprises a third difference between an angle of an elbow of the occupant and a desired angle of the elbow of the occupant.

12. A method, comprising:

capturing images of a driver of a vehicle via a vehicle camera;

determining a current posture of the driver based on the captured images based on a relative position of the driver's body to a seat and a relative position of the driver's body to a steering wheel including a first clearance of the steering wheel and a torso of the driver and, a second clearance of the steering wheel and a thigh of the driver, and an angle of an elbow of the driver;

determining a recommended posture for the driver based on the captured images;

determining differences between the current posture and the recommended posture and outputting postural guidance based on the differences.

13. The method of claim 12, wherein the recommended posture is based on body measurements of the occupant determined from the captured images.

14. The method of claim 13, wherein the recommended posture includes a desired position for the seat and a desired position of the occupant relative to the seat based on the body measurements determined from the captured images.

15. The method of claim 12, further comprising adjusting a position of the seat for an ingress and an egress of the driver based on the body measurements determined from the captured images.

16. The method of claim 15, wherein adjusting the position of the seat for the ingress and the egress is performed based on identifying the driver from the captured images and using stored position data.

17. The method of claim 12, wherein determining the current posture of the driver comprises a hip angle and a knee angle.

* * * * *